(12) United States Patent
Bernard

(10) Patent No.: US 7,635,742 B2
(45) Date of Patent: Dec. 22, 2009

(54) MODIFIED ISOCYANATES

(75) Inventor: Jean-Marie Bernard, Mornant (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 10/608,090

(22) Filed: Jun. 30, 2003

(65) Prior Publication Data

US 2004/0073046 A1 Apr. 15, 2004

Related U.S. Application Data

(63) Continuation of application No. 09/822,291, filed on Apr. 2, 2001, now abandoned, which is a continuation-in-part of application No. PCT/FR99/02350, filed on Oct. 1, 1999.

(30) Foreign Application Priority Data

Oct. 2, 1998 (FR) .................................. 98 12389

(51) Int. Cl.
 C08G 18/80 (2006.01)
 C07D 317/08 (2006.01)
 C07D 317/36 (2006.01)
 C07D 321/00 (2006.01)
 C07C 265/00 (2006.01)

(52) U.S. Cl. .............................. 528/45; 528/73; 528/74; 252/182.2; 252/182.21; 252/182.22; 540/202; 544/67; 544/222; 548/951; 548/952; 549/228; 549/229; 560/25; 560/26; 560/115; 560/157; 560/158; 560/330; 560/335

(58) Field of Classification Search .................... 528/45, 528/73, 74; 252/182.2, 182.21, 182.22; 540/202; 544/67, 222; 548/951, 952; 560/25, 26, 560/115, 157, 158, 330, 336, 335; 564/32, 564/38, 44; 549/228, 229
See application file for complete search history.

(56) References Cited

U.S. PATENT DOCUMENTS

| 5,350,825 | A | 9/1994 | König et al. | |
| 6,544,593 | B1 * | 4/2003 | Nagata et al. | ............ 427/385.5 |
| 6,607,646 | B2 * | 8/2003 | Gam | .......................... 204/489 |
| 6,825,361 | B2 * | 11/2004 | Gam | .......................... 549/229 |

FOREIGN PATENT DOCUMENTS

| EP | 0337926 | | 10/1989 |
| EP | 0419114 | | 3/1991 |
| JP | 5-98168 | | 4/1993 |
| WO | WO 00/55263 | * | 9/2000 |

OTHER PUBLICATIONS

Chemical Abstracts, vol. 119, No. 20, Nov. 15, 1993, Columbus, Ohio, XP002123895.

* cited by examiner

*Primary Examiner*—Rabon Sergent
(74) *Attorney, Agent, or Firm*—Buchanan, Ingersoll & Rooney P.C.

(57) ABSTRACT

Modified stable polyisocyanates are described having at least one isocyanate function modified by a group having cross-linking functionality. The modified stable polyisocyanates may be prepared by reacting at least one polyisocyanate with a compound of the formula:

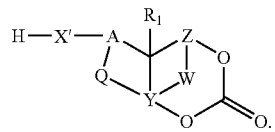

34 Claims, No Drawings

MODIFIED ISOCYANATES

This application is a continuation of U.S. application Ser. No. 09/822,291, filed Apr. 2, 2001, now abandoned, which in turn, is a continuation-in-part of International Application No. PCT/FR99/02350, filed on Oct. 1, 1999, which designates the United States of America and was published under PCT Article 21(2), which International Application was not published by the International Bureau in English on Apr. 13, 2000, and claims benefit of French Application 98 12389, filed on Oct. 2, 1998. These applications are all incorporated by reference in their entirety.

The present invention relates to novel modified isocyanate derivatives and compositions containing the same. It relates more particularly to novel isocyanate derivatives comprising at least one isocyanate function modified with a group having crosslinking functionality and to compositions containing the same.

The invention also relates to a process for preparing these derivatives or compositions, and to the use of these derivatives and compositions in the manufacture of coatings.

The present invention relates in particular to monomer, oligomer or polymer compounds and mixtures thereof bearing isocyanate functions, at least one of which is modified with a group with crosslinking functionality, the crosslinking functional group also being known as a crosslinking functional arm. The present invention relates more specifically to polyisocyanates in which at least one isocyanate functional group is modified with a group as defined above.

The present invention also relates to processes for obtaining these novel derivatives of modified polyisocyanates. It is also directed towards the use of the above derivatives in compositions that are useful for preparing polymers, in particular polycondensates and reticulates derived from the reaction of said polyisocyanates with suitable nucleophilic co-reagents. This preparation is the one which is exploited in industrial applications, such as coatings of any kind, in particular those on textiles, glasses, papers, metals, building materials and paints.

It is known practice to mask isocyanate functions with agents known as "masking" agents, which are sometimes referred to as "blocking agents".

The purpose of masking isocyanate functions (this masking sometimes referred to as blocking), or even its necessity, is explained by the excessive reactivity at room temperature of the isocyanate towards certain co-reagents or towards a reactive solvent, or of a phase, which is generally continuous, and which is a support phase in the case of emulsions or suspensions such as water. This high reactivity is often very problematic, especially for certain applications of polyurethanes, in particular in paints, since it demands separate packaging and occasionally handling of the isocyanate comonomer. This results in inconvenient implementation.

What is conventionally known as a "masking agent" for an isocyanate function to a compound that is capable of masking this function at low temperature to prevent it from reacting with a group, and that comes off at high temperature to restore the isocyanate function initially present.

The "crosslinking" modifier group of the present invention does not constitute such a group, since it does not come off under the conditions for crosslinking the isocyanate function with which the compound which bore it has reacted.

On the other hand, this group is capable under suitable conditions of liberating a functional group which is in turn capable of reacting with a reactive function to give especially a crosslinking reaction.

One object of the present invention is to provide novel isocyanate derivatives that are capable of reacting with a suitable nucleophilic group and of giving various foam reticulates without, however, having the drawbacks of the free isocyanate groups.

Another aim of the present invention is to provide isocyanates comprising a crosslinking functional group or arm, which are nontoxic or only sparingly toxic.

Another object of the invention is to provide novel modified isocyanate derivatives comprising at least one crosslinking functional group, which are economical to prepare.

Another object of the invention is to provide novel isocyanates comprising a crosslinking functional group, giving access to optionally crosslinked polymers (or rather to polycondensates), which satisfy the specifications for the applications.

Another object of the invention is to provide a process for preparing polymers and/or reticulates from said modified isocyanates, comprising a crosslinking group as defined above.

The use of cyclic carbonates as foam expanders, obtained from organic polyisocyanates, in particular from aromatic polyisocyanates, is known from EP 0 419 114.

Under the conditions for using the cyclic carbonates used in said document, especially comprising the use of a basic catalyst, the carbonates react with the isocyanate group of the polyisocyanate compounds, where necessary in the presence of a polyol, with concomitant release of $CO_2$, which causes expansion of the foam, which may be of polyurethane type.

EP 337 926 discloses, in the broad sense, aqueous emulsions of linear polymers, the polymers being of varied nature and comprising at least two chain-end cyclocarbonate groups intended to allow extension of the chain by reaction with an epoxy group.

The inventors' research has now made it possible to discover, surprisingly, chat cyclic carbonates can produce, by reaction with polyisocyanates, not a foam but stable modified polyisocyanates bearing a cyclic carbonate group, which, by subsequent reaction with a compound bearing a reactive hydrogen, led to coatings for nonexpanded industrial structures, in particular paints or varnishes.

In addition, the polyisocyanates thus modified can give, by reaction with a reactive nucleophilic molecule, crosslinking reactions with consumption of an alcohol function.

The objects of the invention and others which will become apparent hereinbelow are achieved by means of isocyanates, advantageously diisocyanates, preferably modified polyisocyanates, of formula I below:

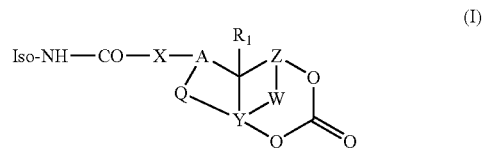

(I)

in which:

Iso is a (poly)isocyanate residue (after having disregarded an isocyanate function);

X represents an atom or a group of atoms resulting from the reaction of a compound bearing a —X'H group, where X' represents X or —OCOX, optionally after decarboxylation when X' represents OCOX with the isocyanate function;

A represents a bond or a linear, branched or cyclic hydrocarbon-based chain containing from 1 to 30, advantageously from 1 to 18 and preferably 1 to 5 carbon atoms;

$R_1$ represents H or a $C_1$-$C_6$ alkyl group;

Q is absent or represents an oxygen or sulfur atom or a hydrocarbon-based chain as defined for A;

Z represents a bond or a hydrocarbon-based chain as defined for A;

Y represents a bond or a hydrocarbon-based chain as defined for A;

W is absent or represents an oxygen or sulfur atom or a hydrocarbon-based chain as defined for A; and Q being obviously absent when Y or A represents a bond and W or A being obviously absent when Y or Z represents a bond;

with the proviso that Z and Y do not simultaneously represent a bond.

It is preferred that neither one or only one of Q and W is present.

The compounds as defined above are chemically stable for a period of more than one day, advantageously more than one week, preferably more than one month and more preferably more than three months under usual storage conditions and in the absence of reactive nucleophilic compounds.

The expression "hydrocarbon-based chain" means a chain comprising carbon and hydrogen atoms and optionally interrupted with one or more hetero atoms, especially from columns IV, V and VI and in particular IV A, V A and VI A of the Periodic Table of the Elements (O, S, Si, etc.) or hetero groups (—NH, —N (substituted)) or substituted with one or more groups selected in particular from aryl, cycloalkyl, heteroalkyl, halogen (in particular fluorine), a linear or branched halogenated (in particular fluorinated) or perhalogenated (in particular perfluorinated) carbon-based chain and a carboxyl, primary or secondary amino, $NO_2$ or CN group.

For the definition of the Periodic Table, reference will be made to the Merck Index, 10th edition (Merck and Co, Rahway, Martha Windholz, Susan Budavari, ed.).

The hydrocarbon-based chain may be linear or branched, or even cyclic.

It may be saturated or unsaturated.

Mention may be made especially of alkylene or particularly polymethylene —$(CH_2)_n$— chains, n generally being 1 and 12, which may be unsubstituted or substituted with groups as defined above.

X may in particular represent the following functions:

—O,

—S,

=N,

—NR, in which R represents a hydrogen atom or a hydrocarbon-based group generally containing from 1 to 12 and preferably from 1 to 5 carbon atoms, optionally interrupted with hetero atoms or hetero groups as defined above or optionally bearing substituents as defined above,

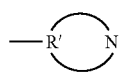

in which R' represents a 4- to 10-membered hydrocarbon-based chain as defined above which is optionally interrupted with one or more hetero atoms (in particular from columns IV A, V A and VI A of the Periodic Table of the Elements) such as O, S or Si or hetero groups selected in particular from —N= and —NR— (R being as defined above) and/or substituted with one or more substituents as defined above, the chain R' forming with NH a nitrogen ring, advantageously a polynitrogen and preferably a dinitrogen ring, such as a piperazino ring,

—CO—NR,

—NR—COO,

—COO,

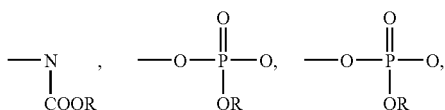

a hydrocarbon-based, preferably a linear or branched alkylene chain comprising from 1 to 12, preferably from 1 to 7 carbon atoms, optionally interrupted with hetero atoms or hetero groups as defined above or bearing substituents as defined above, or A'-COO—, where A' is a hydrocarbon based chain preferably a linear or branched alkylene chain as defined above, the —COO— group being linked to the -A- group as d fined above,

—NH—CO—NH,

—NH—CO—NR,

R being as defined above.

The above listed groups are linked to the —NH—CO— group by their left side and to the A group by their right side).

Advantageously, in the isocyanate derivatives according to the invention, at least one, advantageously two, more particularly three and preferably all of the following conditions are satisfied:

X represents an oxygen atom, or a $C_1$-$C_{12}$ alkylene chain or a $(C_1$-$C_{12})$alkylene-COO— chain, A represents a —$CH_2$— group, Y represents —$CH_2$—, Z represents a bond or —$CH_2$—, preferably a bond, W and Q are absent, $R_1$ represents H or a $C_1$-$C_6$ linear or branched alkyl group.

When W and Q are absent, compounds of formula (I) are monocyclic and the compound of formula I is Ia:

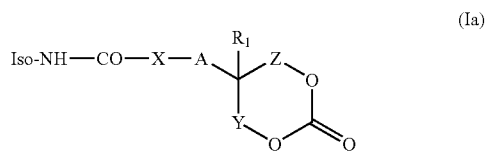

wherein Iso, X, A, Z, Y and $R_1$ are as defined above.

One crosslinking group which is preferred is the one obtained by reacting an isocyanate function with glyceryl carbonate.

Another group which is preferred is the one obtained by reacting an isocyanate function with fatty acid carbonates or esters thereof, such as oleic acid 8,9-carbonate.

As mentioned above, the isocyanates concerned may be monoisocyanates, diisocyanates or even polyisocyanates.

Among the modified isocyanate derivatives according to the invention are:
diisocyanates;
isocyanate compounds, in particular polyisocyanates comprising an isocyanurate group, which are also known as trimers;
isocyanate derivatives, in particular polyisocyanates comprising at least one uretidinedione group, which are also known as dimers;
isocyanate derivatives, in particular polyisocyanates comprising at least one biuret group:
isocyanate derivatives, in particular polyisocyanates comprising at least one carbamate group;
isocyanate derivatives, in particular polyisocyanates comprising at least one allophanate group;
isocyanate derivatives, in particular polyisocyanates comprising at least one ester group;
isocyanate derivatives, in particular polyisocyanates comprising at least one amide group;
isocyanate derivatives, in particular polyisocyanates comprising at least one urea function;
isocyanate derivatives, in particular polyisocyanates comprising at least one iminocyclooxadiazinedione function;
isocyanate derivatives, in particular polyisocyanates comprising at least one cyclooxadiazinetrione function;
isocyanate derivatives, in particular polyisocyanates comprising at least one masked isocyanate group;
isocyanate derivatives, in particular polyisocyanates comprising a combination of one or more of the groups which have just b en mentioned, in particular an isocyanurate group.

The expression "polyfunctional isocyanate tricondensates" will be used more generally to denote the products obtained by (cyclo)condensation, in particular cyclo(trimerization), of one or more identical or different isocyanate monomers and optionally of another monomer.

More generally, these compounds comprise an isocyanurate group or a biuret group.

In general, the (poly)isocyanates of the invention have a molecular weight of less than 7 500, advantageously lens than 3 500 and preferably less than 2 500.

The isocyanate monomers forming part of the composition of the various modified compounds mentioned may be aliphatic, cycloaliphatic or arylaliphatic.

The modified polyisocyanates as defined above may consist of products of condensation of identical or different isocyanate molecules, in which case they will be referred to, respectively, as homopolyisocyanates and heteropolyisocyanates, or alternatively as mixtures of different homopolyisocyanates and/or of different heteropolyisocyanates.

The preferred polyisocyanates targeted by the invention are those in which at least one, advantageously two and preferably three of the conditions below are satisfied:
at least one and advantageously two of the free NCO functions which have reacted with the crosslinking group according to the invention are linked to a hydrocarbon-based skeleton via a saturated ($sp^3$) carbon;
at least one and advantageously two of said saturated ($sp^3$) carbons bears at least one and advantageously two hydrogen(s) (in other words, it has been found that better results are obtained when the carbon bearing the isocyanate function bears a hydrogen and preferably two hydrogens), it is also even preferable for at least a third, advantageously at least a half and preferably at least two thirds of said saturated ($sp^3$) carbons to be linked to said skeleton via a carbon atom which itself bears at least one and preferably two hydrogen(s);
all the carbons via which the isocyanate functions are linked to the hydrocarbon-based skeleton are saturated ($sp^3$) carbons, advantageously some and preferably all of which bear a hydrogen and preferably two hydrogens; it is also even preferable for at least a third, advantageously at least a half and preferably at least two thirds of said saturated ($sp^3$) carbons to be linked to said skeleton via a carbon atom which itself bears at least one and more preferably two is hydrogen(s).

In accordance with one advantageous embodiment of the invention, the polyisocyanates whose NCO functions are modified with a crosslinking group as defined are selected from the products of homocondensation or of heterocondensation of alkylene diisocyanate, in particular comprising products of the "biuret" type and of the "trimer" type, or even "prepolymers" containing isocyanate functions in particular comprising urea, urethane, allophanate, ester and amide functions, and from mixtures containing them.

They may be, for example, polyisocyanates sold by the Applicant Company under the name "Tolonate".

In general, the polyisocyanates that are preferred are the products of homocondensation or of heterocondensation of the following isocyanate monomers:
polymethylene diisocyanates and in particular 1,6-hexamethylene diisocyanate, 2-methyl-1,5-penta-methylene diisocyanate, 2,4,4-trimethyl-1,6-hexa-methylene diisocyanate, 3,5,5-trimethyl-1,6-hexa-methylene diisocyanate, 1,12-dodecane diisocyanate and isocyanato (4)-methyl-1,8-octylene diisocyanate (TTI or NTI);
cyclobutane 1,3-diisocyanate, cyclohexane 1,2-, 1,3- or 1,4-diisocyanate, 3,3,5-trimethyl-1-isocyanato-5-isocyanatomethylcyclohexane (isophorone diisocyanate, IPDI), bis(isocyanato)methylnorbornane (NBDI), 1,3-bis(isocyanatomethyl)cyclohexane (BIC), $H_{12}$-MDI and cyclohexyl 1,4-diisocyanate;
arylenedialkylene diisocyanates such as OCN—$CH_2$-Ø-$CH_2$—NCO; or aromatics such as tolylene diisocyanate.
Aromatic isocyanates are not preferred.

When the polyisocyanates are relatively heavy, i.e. when they comprise at least four isocyanate functions, at least one isocyanate function advantageously being modified with a crosslinking group as defined above, or when there is a mixture of several compounds bearing isocyanate function(s), the first conditions become:
at least a third, advantageously two thirds and preferably four fifths of the NCO functions which are free or which comprise a crosslinking group as defined above are linked to a hydrocarbon-based skeleton via a saturated ($sp^3$) carbon,
at least a third, advantageously two thirds and preferably four fifths of said saturated ($sp^3$) carbons bears at least one and advantageously two hydrogen(s) (in other words, it has been found that better results are obtained when the carbon bearing the isocyanate function bears a hydrogen and preferably two hydrogens).

It is also even preferable for at least a third, advantageously at least a half and preferably for at least two thirds of said saturated ($sp^3$) carbons to be linked to said skeleton via a carbon atom which itself bears at least one and advantageously two hydrogens.

Mixtures for which virtually all of the isocyanate functions which are free or which comprise a crosslinking group as defined above satisfy the above criteria are particularly targeted.

The unmodified isocyanate functions according to the present invention may b either free or masked with a common heat-labile masking group.

For the purposes of the invention, the term "masking agent" refers to a group reacting with an isocyanate function such that the masked isocyanate compound shows at a temperature of at least 50° C., advantageously at least 60° C. and preferably at least 70° C. and of not more than 350° C., advantageously not more than 250° C. and preferably not more than 200° C., the highest temperatures being reserved for flash crosslinking processes, and after a period of heating of between a few seconds and a few hours, advantageously between 10 seconds and 20 minutes, a "liberation" of the masking group at least equal to 50%, in the octanol test, the procedure of which is described later.

In general, a masked isocyanate compound is considered as being any compound which leads to the liberation of the masking agent with regeneration of the isocyanate bond or conversion of this bond into a urethane bond if a primary or secondary aliphatic alcohol is present, or into a urea bond if a primary or secondary aliphatic amine function is present.

In the presence of active or latent catalysts which may be activated thermally or by oxidation, the liberation kinetics are accelerated or the temperatures for regenerating the isocyanate function (by liberating the masking group) are lowered.

By way of example, when the masking group is imidazole, the octanol test gives a degree of liberation of 50% with respective formation of 50% corresponding octyl carbamate at 80° C. and 100% at 100° C., 2-hydroxypyridine giving respective degrees of 90% and 100% at these temperatures.

In the presence of 0.1% by weight of dibutyltin, the degree of unblocking of the imidazole at 80° C. in increased to 90%.

Mention may be mad in particular of masking groups of (poly)nitrogen heterocycle type, such as imidazole, pyazole, 1,2,3-triazole or 1,2,4-triazole, said heterocycles possibly bearing substituents; or alternatively lactams, optionally substituted phenols such as para-hydroxybenzoates and oximes, in particular methyl ethyl ketoxime (MEKO), methyl pyruvate oxime, ethyl pyruvate oxime (MEPO) and cyclohexanone oxime.

The masking groups optionally comprise acidic ionic functions such as carboxylic acid or sulfonic acid functions or basic ionic functions such as tertiary amine functions. These ionic groups are of most particular advantage since they facilitate the preparation of certain types of formulation such as the production of powders, dispersions or aqueous solutions.

In one advantageous embodiment, the polyisocyanates or, more exactly, the polyisocyanate composition of the invention, comprises at least two different masking groups selected such that, in the octanol test at 110° C., the ratio $$D = \frac{\text{percentage of masking agent unblocking first at } 110° \text{C.}}{\text{percentage of masking agent unblocking last at } 110° \text{C.}}$$

is greater than 4/3, advantageously greater than 1.5 and preferably greater than 2.

The masking groups may be, in particular, an oxime and triazole (1,2,3-triazole or 1,2,4-triazole), the oxime advantageously being methyl ethyl ketoxime, methyl amyl ketoxime, methyl pyruvate oxime or ethyl pyruvate oxime.

The modified isocyanate derivatives according to the invention are in liquid form or in powder form.

The modified isocyanate derivatives according to the invention may be prepared by carrying out procedures chat are well known to those skilled in the art, by condensing a compound of general formula (II):

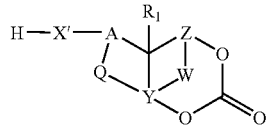

in which $R_1$, A, Q, Y, Z and W have the same specifications as above, and X' represents X or OCOX, X being as specified above with an isocyanate.

Where appropriate, the reactive functions of the compound of general formula (II) other than XH are protected with a suitable protecting group and subsequently deprotected.

Thus, the modified isocyanates according to the invention may be obtained:

when X represents an oxygen or sulfur atom, by condensing the isocyanate compound which it is desired to modify with an compound of general formula I as defined above in which X represents O or S, with heating, optionally in the presence of a catalyst in the presence or absence of solvent, the solvent possibly being in particular an eater, an ether or an aromatic hydrocarbon, when X represents a group NR as defined above, by condensing with an isocyanate compound at room temperature or with heating, in a common solvent.

when X represents an alkylene group as defined above by reaction of a compound of formula II bearing an acidic, preferably carboxylic function with an isocyanate at room temperature, followed by a decarboxylation according to the following reaction scheme:

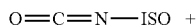

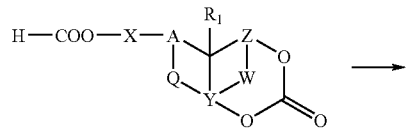

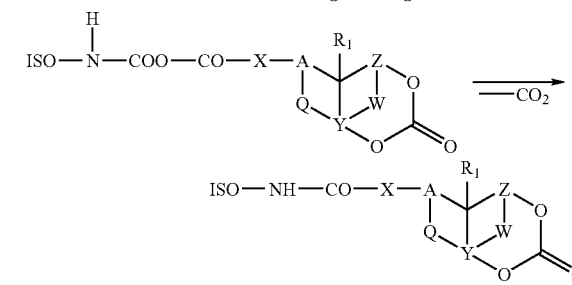

The above described route is particularly interesting in that it leads to very stable compounds.

Where appropriate, the isocyanates are reacted, before or after reaction with a compound of general formula (II) as defined above, with a masking agent under suitable reaction conditions.

The isocyanates may also be reacted with a mixture of compounds of general formula II and of masking agents under suitable reaction conditions, that are known to those skilled in the art.

The compounds of the invention may also be prepared by mixing the isocyanate compounds with compounds that are precursors of the molecule (II) such as vicinal diols and activated carbonylating agents, the carbonyl-activating molecules, liberated after the carbonate-forming reaction, possibly serving where appropriate as agents for masking the isocyanate function. Examples which may thus be mentioned are activated carbonyl compounds such as carbonyl-diimidazole, carbonylbis (1,2,4-triazole), carbonyl-bis methyl ethyl ketoxime) and N,N'-disuccinimidyl carbonate. The compounds liberated after reaction with the diol and formation of the carbonate, such as imidazole, 1,2,4-triazole or methyl ethyl ketoxime, are known as agents for masking isocyanate functions.

One group of modified isocyanates which is preferred according to the invention consists of the diisocyanate derivatives au mentioned above, comprising at least some of the isocyanate functions, preferably at least 100% to 1% and advantageously 100% to 30%, by weight, modified with a crosslinking group as defined above, at least 1%, advantageously at least 5% and preferably 10%, and up to 99%, advantageously up to 95% and preferably up to 70%, by weight, of the isocyanate functions, modified with a masking group as defined above.

These isocyanate derivatives have applications in particular in the form of powders or may be used in aqueous medium.

The polyisocyanate compositions that are the subject of the present invention may consist of a mixture comprising at least 1% and not more than 99%, preferably at least 10% and not more than 90%, of a polyisocyanate predominantly bearing the crosslinking group of the invention and at least 1% and not more than 99%, preferably at least 10% and not more than 90%, of another polyisocyanate predominantly bearing a crosslinking group and/or another molecule derived from a diisocyanate bearing free and/or masked isocyanate functions and containing no crosslinking groups.

In a particularly advantageous manner, the crosslinking group and the free and/or masked NCO group are borne by the same (poly)isocyanate molecule.

Preferably, the (poly)isocyanate composition of the invention comprises no carboxylic groups borne by a molecule of formula I as defined above.

However, the agents for masking the isocyanate functions may bear ionic groups and in particular carboxylic or tertiary amine group, these ionic groups possibly being partially or totally salified.

The compounds may retain free isocyanate functions, in particular at least 1%, advantageously at least 5% and preferably at least 10%, and up to 99% and advantageously up to 70%, by weight.

A second group of modified isocyanatee which is preferred according to the invention consists of mixtures of polyfunctional isocyanate tricondensates, which are preferably true isocyanates (derived from the theoretical (cyclo)trimerization of three isocyanate monomer molecules and optionally other monomers and comprising an isocyanurate and/or biuret ring) and of allophanates, and/or dimers and/or ureas, urethanes, biurets or carbamates comprising at least some, preferably at least 1% to 100% and advantageously 30% to 100% by weight of the isocyanate functions modified with a crosslinking group as defined above.

The compounds may retain free isocyanate functions, in particular from 1% to 99% and advantageously from 5% to 70% by weight.

A third group of compounds which is preferred consists of physical mixtures of several polyfunctional isocyanate tricondensates, with allophanates, uretinediones or dimers, comprising from 100% to 1% and advantageously from 70% to 1% by weight of isocyanate groups modified with a crosslinking group, according to the invention and from 1% to 99% and advantageously from 5% to 70% by weight of isocyanate functions masked with a masking group as defined above.

A fourth group of modified isocyanate derivatives according to the invention consists of modified isocyanates comprising free isocyanate groups and/or masked isocyanate groups and also allophanate and/or uretinedione groups.

The compounds may retain free isocyanate functions, in particular from 1% to 99% and advantageously from 5% to 70% by weight.

In the mixtures mentioned above, the various polyfunctional compounds may be derived from the polycondensation of several identical or different monomers.

In the case of mixtures of polyfunctional isocyanates, the various polyfunctional isocyanates may be obtained from different isocyanates or from a mixture of different isocyanates.

For example, a mixture of HDI isocyanates and butyl allophanates and HMDI may be used.

To prepare the compounds of the invention, it is also possible to use the crude mixtures from (cyclo)condensation of the starting isocyanates with themselves (dimerization, trimerization, etc.) before or after partial removal of the unreacted starting isocyanate monomer(s). These crude mixtures are characterized by the fact that the weight percentage of the starting isocyanate monomer(s) relative to all of the products of the mixture is between 1% and 95% and preferably between 5% and 80%.

Similarly, mixtures derived from these crude isocyanate (cyclo)condensation mixtures may be used. The expression "derived mixture" means the product of reaction of the compounds of the crude mixture with nucleophilic compounds or compounds bearing hydroxyl, sulfhydryl or amine functions capable of reacting with the isocyanate functions of the compounds of the mixture.

In general, the isocyanate compositions used are mixtures of various molecules derived from polymerizations or from polycondensation, in which case the explanation which has just been given as to what is preferred above applies with fractional and random values.

The isocyanate functions that are free or liberated by departure of the [lacuna] group may form by condensation with groups containing labile hydrogen, in particular polyols, or polyamines or polysulfhydryls, prepolymers containing pendent carbonate functions and terminal free isocyanate or alcohol or amine or sulfhydryl functions depending on the ratio NCO/XH, X being as defined above.

After opening the crosslinking group with a suitable reagent, the prepolymer thus obtained may be subsequently crosslinked.

The functions which react with the crosslinking group according to the invention are alcohol functions, primary or secondary amine functions, heterocyclic nitrogen compounds containing a reactive hydrogen atom, oximes or phenols, preferably phenates or carboxylates. Aqueous ammonia, primary or secondary amines or nitrogen heterocycles, for example guanidines or salts thereof which react by opening the ring, will preferably be selected.

In order to obtain polyurethane networks or films, these prepolymers may be reacted with amines, preferably diamines or polyamines, which are preferably primary or secondary. Networks are thus obtained containing pendent hydroxyl functions which may be either auto-crosslinked with NCOs present in the medium, or allow grafting or permit a crosslinking reaction with mixtures that are reactive with these functions.

Similarly, these products bearing free isocyanate and carbonate functions may be reacted with amines to give polyurea urethane networks containing pendent hydroxyl and/or carbonate functions. If the amount of isocyanate functions is greater than the amount of amines, then the alcohol functions liberated by opening the carbonate ring may react with the excess of isocyanate functions. The speed of opening of the carbonate ring depends on the amine and on the reactivity of the isocyanate with this amine.

In certain cases, the amine will preferentially react with the carbonate function before the isocyanate function. There will thus be the possibility of having a reaction of the isocyanate function with the liberated alcohol functions.

The ring-opening reaction with an amine leads to the generation of a carbamate bond by liberating a free OR function (of primary alcohol type only, in the compound of general formula I, Z is other than a bond, and of primary alcohol and/or secondary alcohol type if in the compound of general formula I, Z is a bond, in particular in the case of glyceryl carbonate).

In certain cases, the alcohol function liberated may be tertiary, but, in this case, its reactivity is low and it is not preferred.

The free OH function may in turn react at a given temperature with an isocyanate function, which is optionally blocked, with departure of the blocking group to give a network rapidly, in particular when the free or blocked isocyanate groups are borne by a polyfunctional isocyanate, a dimer, a trimer or a prepolymer.

The hydroxyl function liberated may also react with other compounds which may be present in a formulation using the compounds of the invention. Examples which may thus be mentioned are acid anhydrides or acidic compounds which may react with the hydroxyl function liberated to give an ester or an acid ester.

The isocyanate functions that are free or liberated by departure of the blocking group may react with any type of compound containing labile hydrogen, in particular alcohols, thiols, urethanes, etc., depending on the crosslinking temperature used.

Another advantageous possibility consists in opening the ring of the crosslinking group with a polyalkoxylated amine, in particular a polyethoxylated amine, so as to obtain a condensation product which has good emulsifying properties. This type of compound is particularly advantageous in the context of subsequent emulsion polymerization reactions, in particular by reaction with an isocyanate group which is free or liberated by departure of a blocking group.

Salts, preferably amine salts, preferably of weak acids, also react with the isocyanate and/or carbamate functions depending on the temperature imposed by the crosslinking.

As regards salts, a salt of a weak acid with a pKa of greater than 2.5 will preferably be selected if the crosslinking temperature is less than 80° C. For higher crosslinking temperatures, acid salts with pKa values of less than 3 may be used. A compound capable of neutralizing the salt of the amine which is reactive with a base capable of exchanging ions and liberating the amine, which, since it is nucleophilic, is then capable of opening the ring, may be also be introduced. Bases which may be mentioned are metal hydroxides (sodium hydroxide, potassium hydroxide, etc.), tertiary amines (triethylamine, trio-cylamine, N,N-dimethyl-aminoethanol, etc.), metal alkoxides (sodium methoxide, etc.) and alkaline salts of weak acids (sodium acetate, sodium hydrogen carbonate, potassium carbonate, etc.).

Amine salts have the advantage of having an improved "pot-life" due to the decrease in reactivity of the corresponding amine.

When isocyanate compounds modified according to the invention also comprising free isocyanate groups are reacted, care will be taken to select the isocyanates so as to promote either the reaction of the amine with the isocyanate, or the reaction of the amine with the carbonate. This selectivity may be increased by varying the temperature, the catalyst or the steric bulk of the amine and/or of the isocyanate.

It is also advantageous to use amine-precursor compounds which may restore the amine by a chemical or physical process, such as, for example, imines, oxazolines or oxazolidines, which, on hydrolysis, liberate the amine which can then open the carbonate ring.

Mention should be made of the particular case of isocyanate molecules which also constitute masked forms of amines and which can, on hydrolysis, restore the amine function. These isocyanates may be simple isocyanates (only one isocyanate function per molecule).

IPDI will advantageously be selected.

The products of the invention bearing optionally masked isocyanate functions and carbonate functions may also be used in unmodified form.

Depending on the $CO_2$ content and on the crosslinking kinetics, nonexpanded coatings are, surprisingly, obtained, in particular coatings such as paints or varnishes, with a film thickness which is not greater than 100 μm, and which may have a matt, satin or glossy appearance depending on the implementation conditions.

The modified isocyanates according to the invention give, at a high temperature above 100° C., oxetane compounds with release of $CO_2$. These oxetane compounds may be used as crosslinking agents with polyols or polyamines, preferably polyols, in situ in the film.

After opening the carbonate with an amine, derivatives are obtained containing at least two alcohol functions, which may be used to prepare polymers or to introduce particular properties into a polymer, for example to make it self-emulsifying if the carbonate functions have been opened with a polyoxyethylenated amine, or to give an "anti-graffiti" or "mar-resistance" coating if the carbonate functions have been opened with an aminosilicone or perfluoroamine.

After opening the carbonate ring with water or basic aqueous solutions, the isocyanate derivatives according to the invention can also give tetra-functional polyols which may be used as crosslinking agents, in particular on account of the double reactivity due to the presence of primary and secondary alcohol functions.

In general, the modified isocyanate derivatives according to the present invention have the advantage of high and controlled reactivity and high crosslinking power, the properties being obtained by adding an arm which provides only a small increase in the molecular weight of the starting isocyanate.

Similarly, the polyisocyanate derivatives containing pendent urethanecarbonate functions may lead to the formation of allophanates containing pendent carbonate functions.

One of the many advantages of the novel polyisocyanates according to the invention is that they may serve as a basin for the preparation of polymers and/or reticulates that are useful, for example, as main constituents of coatings of any kind, such as paints. In such uses, the hardness qualities of the crosslinkable polymers are among the qualities that are desired from a technical and functional viewpoint.

In the case of aqueous formulations, the polyisocyanates containing a crosslinking function of the invention may be emulsified by means of various compounds such as surfactants or polyols of emulsifiable nature or may be made water-soluble by grafting nonionic functions such as polyalkylene oxide or acidic ionic functions such as those of para-hydroxybenzoic acid (PHBA), dimethylolpropionic acid, sulfamic acid and phosphoric derivatives or of basic ionic functions ouch as N,N-dialkylhydroxylalkylamines, in particular N,N-dimethylethanolamine or guanidine derivatives.

The grafting may be carried out reversibly (PHBA) or irreversibly.

According to one aspect, a process is provided for preparing a modified isocyanate, including the following steps: a) reaction of an isocyanate, which is optionally a polyisocyanate and/or which comprises a group selected from carbamate, urea, biuret, uretidione, isocyanurate, urethane and allophanate groups, with a compound of general formula II; and b) isolation of the product obtained.

According to another aspect, a process is provided for preparing a modified isocyanate, including masked isocyanate functions, including the following steps: either, in any order: $a_1$) reaction of an isocyanate, which is optionally a polyisocyanate and/or which comprises a group selected from carbamate, urea, biuret, uretidione, isocyanate, urethane and allophanate groups, with a compound of general formula II; and b) simultaneous or successive reaction with at least one masking compound; or $a_2$) simultaneous reaction of an isocyanate with a compound of general formula II and at least one masking compound; and b) isolation of the product obtained.

The invention will be understood more clearly and its variants and other advantages will emerge from the examples which follow.

Octanol Test

Procedure:

About 5 mmol equivalent of protected masked NCO to be evaluated are placed in a Schott tube with magnetic stirring.

2.5 to 3 ml of 1,2-dichlorobenzene (solvent) and the equivalent of 1-octanol (5 mmol, i.e. 0.61 g, optionally with the catalyst to be tested with the masking group) are added.

The reaction medium is then brought to the test temperature. It is then heated for a given period, generally for mix hours, except where otherwise indicated, at the test temperature, so as to unblock the isocyanate functions and thus make them reactive. Once the reaction is complete, the solvent is removed by distillation under vacuum and the residue is analyzed by NMR, mass and infrared spectra.

From these data, the percentage of masked isocyanate function condensed with 1-octanol and thus the percentage of masking agent liberated are evaluated.

EXAMPLES

Example 1

Synthesis of HDI Butyl Allophanate 4 787 g of HDI are introduced into a 6 l three-necked reactor. 527.1 g of 1-butanol are added over 45 minutes. The reaction medium is heated such that the temperature obtained after 45 minutes following the start of addition of the butanol is 125° C. About 1.3 g of dibutyltin dilaurate are then added and the temperature of the reaction mixture is raised to 140° C.

After reaction for 5 hours, the NCO titer measured is 0.786 as opposed to 1.19 for the starting HDI. The excess HDI is removed by two successive distillations under a vacuum of 0.5 mmHg at 140° C., with a flow rate of between 400 and 1 000 g/hour.

The distilled product has an NCO content of 0.405, i.e. 17% by weight, and a viscosity at 25° C. of 140 mPa·s$^{-1}$. The HDI content is 0.4%.

Example 2

Synthesis of an Allophanate of HDI and of n-butyl, Masked with Triazole and Glyceryl Carbonate The following are successively introduced into a jacketed reactor:
  350 g of hexamethylene diisocyanate butyl allophanate of Example 1, for which the content of isocyanate function is 0.405, i.e. 17% by weight of NCO function per 100 g of product; and
  51.4 g of 1,2,4-triazole.

The reaction mixture is heated such that it reaches 113° C. over 20 minutes. The 1,2,4-triazole is then completely consumed.

At this moment, 83.6 g of glyceryl carbonate and 3 g of triethylamine are added. Exothermicity occurs, which causes the temperature to rise to 131° C. The reaction is then continued at 110° C. for about 3 hours.

By infrared analysis, it is found that the free isocyanate functions are virtually negligible, which indicates an almost quantitative reaction of these functions.

The product is then poured into a container and left to cool (488 g).

The cold product is a viscous liquid which does not flow, indicating a viscosity of greater than 10 000 mPa·s$^{-1}$ at 25° C.

Example 3

Synthesis of a Polyisocyanate Containing Isocyanurate Functions, a Portion of the Isocyanate Functions of which in Masked with Triazole And Another Portion of the Isocyanate Functions of which is Modified with Glyceryl Carbonate The following are successively introduced into a three-necked reactor:
  350 g of HDT (HDI trimer) whose content of isocyanate functions is 0.525, i.e. 22% by weight;
  63.2 g of 1,2,4-triazole; and
  after reaction for 25 minutes, 1.5 g of triethylamine.

The mixture is heated from the moment of addition of the 1,2,4-triazole. The mixture reaches a temperature of 99° C. after 45 minutes.

At this moment, 108 g of glyceryl carbonate and 1.5 g of triethylamine are added.

The temperature of the mixture is raised to 123° C. and the latter is then left to react for about one hour until the titer of free isocyanate (NCO) functions is virtually zero.

The product is removed and then left to cool (product obtained: 524.2 g theoretical, 517 g measured). The cold product is a solid, which is then ground, and whose content of potential isocyanate functions is 7.35% by weight and whose content of carbonate functions (—O—C(O)—O) is 10.48% by weight. The modified NCO/O—C(O)—O molar ratio is 1.

Example 4

Synthesis of a Polyisocyanate Containing Isocyanurate Functions, whose Isocyanate Functions are Modified with Glyceryl Carbonate 300 g of HDT tolonate and 184.4 g of glyceryl carbonate are introduced into a 500 ml round-bottomed flask and the reaction medium is then heated to 86° C. The product is then removed and, after cooling, is ground to give a powder whose NCO titer is 0.001 and whose content of carbonate functions (—O—C(O)—O) is 19.3% by weight, i.e. 0.3 mol of carbonate functions (—O—C(O)—O) per 100 g of product.

1H NMR analysis indicates the presence of 54% modified trimer (including dimer), 8.5% modified biuret and 0.39% free glyceryl carbonate.

The characteristic infrared bands of the products are as follows:

CO carbonate: 1798 cm$^{-1}$
CO carbamate: 1721 cm$^{-1}$
CO isocyanurate trimer: 1685 cm$^{-1}$
Isocyanurate ring: 1468 cm$^{-1}$
CO—NH carbamate: 1531 cm$^{-1}$
NH carbamate: 3362 cm$^{-1}$
in CH$_2$Cl$_2$ medium the allophanate bands are observed:
NH allophanate: 3369 cm$^{-1}$/NH carbamate; 3444 cm$^{-1}$.

Example 5

Synthesis of HDI Modified with Glyceryl Carbonate

The process is performed in the same way as in Example 3. The amount of HDI is 168 g and the amount of glyceryl carbonate in 236 g.

After five hours at 80° C., the content of residual NCO is 0.011. A further two hours at 100° C. give, after removal and cooling, a compound in powder form whose titer of free NCO functions is 0.001 and whose titer of carbonate functions is 44.5%.

Example 6

Synthesis of Succinic Acid Glyceryl Carbonate Monoester 30 ml of toluene, 60.6 g of glyceryl carbonate and 51.3 g of succinic anhydride are successively loaded into a stirred reactor and placed under an inert atmosphere (stream of nitrogen).

The reaction medium is heated at 90° C. for 6 hours and at 120° C. for 2 hours and then stirred for 2 hours.

A liquid extraction is then carried out on the cold reaction medium in a separating funnel. 500 ml of cold (10° C.) aqueous 0.5 M bicarbonate solution and then 200 ml of ethyl acetate are added. The organic phase is removed and washed twice with the same cold (10° C.) aqueous 0.5 M bicarbonate solution.

The aqueous phases are then combined, after which they are acidified with aqueous 1 M HCl solution until the pH of the solution is acidic (pH=2). The aqueous phase is then extracted three times with 500 ml of ethyl acetate. The organic phases are then dried over dry sodium sulfate. After filtration, the solvent is concentrated under vacuum to give a white solid.

The reaction yield is 27% (yield not optimized).

The NMR analysis of the product indicates that the product has the following characteristic bands:

$^1$H NMR (DMSO): succinic CH$_2$ at 2.43 and 2.65/CH$_2$ alpha to the oxygen of the ester function 4.16-4.34/CH$_2$ alpha to the carbonate 4.16-4.34/CH$_2$ alpha to the carbonate 5.01;
$^{13}$C NMR (DMSO): succinic CH$_2$ at 28.7/C=O of the acid function at 173.4/C=O of the ester function at 172.0/C=O of the carbonate function at 154.8/CH$_2$ alpha to the oxygen of the eater function 63.4/CH$_2$ alpha to the carbonate 66.0/CH alpha to the carbonate 74.4.

The structure or the product is also confirmed by infrared analysis.

The melting point of the product is 102-103° C. (Kofler block).

The formula of the compound is the following:

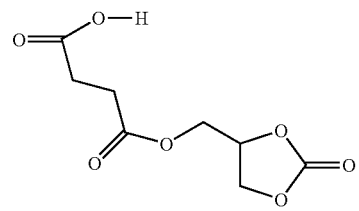

Example 7

Synthesis of a Resin Containing Pendent Carbonate Functions and Essentially Isocyanurate Units, Obtained by Reaction of the Compound of Example 6 and of HDT The HDT used is Tolonate® HDT sold by the company Rhodia, comprising a mixture of compounds of cyclopolycondensation of hexamethylene diisocyanate (HDI) with itself, having the following composition:

| Products | TOLONATE HDT | TOLONATE HDT LV2 |
|---|---|---|
| HDI | 0.2% | 0.24% |
| Butyl monocarbamate | 0.5% | 0.5% |
| True HDI dimer | 2.5% | 14.2% |
| True HDI trimer | 50.1% | 56% |
| Bis trimer + trimer dimer | 24% | 20.6% |
| Heavy fractions | 18.7% | 7.6% |
| Biuret | 4.0% | 0.86% |

The true trimers consist of three HDI chains cyclocondensed on themselves into an isocyanurate ring.

The true dimers consist of two HDI chains cyclocondensed into a uretidinedione ring.

The trimer oligomers plus heavy fractions consist of more than three cyclocondensed HDI chains and of more than one isocyanurate ring. Tolonate® HDT contains free isocyanate functions in a proportion of 22% by weight, generally of NCO functions per 100 g of product.

The process is performed as follows:

14.77 g of Tolonate HDT whose titer, measured by the back-titration method with dibutylamine, is 0.518 mol of NCO function per 100 g of product, are introduced into a reactor equipped with a stirrer and placed under an inert atmosphere of nitrogen. An equivalent molar amount (molar ratio NCO/COOH=1) of succinic acid glyceryl carbonate monoester (obtained as described in the above example) is added to the reaction mixture. Triethylamine (Et$_3$N) is added in a proportion of 1 mol % relative to the carboxylic functions of the monoester (molar ratio Et$_3$N/COOH=0.01). The mixture is then heated and stirred for five hours at 110° C. An evolution of carbon dioxide gas is observed.

The product is recovered.

The product obtained is indeed the expected reaction product and has the following major characteristic infrared bands:

very weak NCO band at 2257 cm$^{-1}$
carbonate C=O band at 1795 cm$^{-1}$
succinate eater C=O band at 1739 cm$^{-1}$
HDT isocyanurate bands at 1685 and 1466 cm$^{-1}$
amide —C=O—NH— band at 1546 cm$^{-1}$ and secondary amide C=O band at 1640 cm$^{-1}$
NH band at 3350-3250 cm$^{-1}$.

The compounds obtained have the following formula:

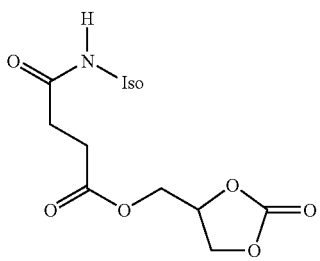

wherein Iso represents an isocyanurate-isocyanate group.

Example 8

Synthesis of a Resin Containing Pendent Carbonate Functions and Essentially Isocyanurate and Uretidinedione Unite, Obtained by Reaction of the Compound of Example 6 with an HDT Composition Comprising HDI Dimer (Tolonate® HDT)

The composition of HDT Tolonate® is that of the table in Example 7. It is obtained as follows:

1 000 g of HDI are introduced into a 1 liter reactor fitted with a condenser column and heated with an oil bath.

The reaction medium is heated for 1 hour 30 at 160° C. 10 g (1% by weight) of HMDZ (hexamethyl-disilazane) are then added. The reaction medium is heated for 30 minutes at 140° C. and then cooled. When the temperature reaches 88° C. 5.5 g of n-butanol are added. After reaction for one hour, the product is purified by distillation under vacuum.

The heavy fractions are compatibilized into tris-trimer. The bis-trimer bulk (major compound) comprises tetramers (trimer-dimer) and imino-trimer.

The resulting composition has a viscosity at 25° C. of 509 cps (509 mPa·s).

Tolonate® HDT LV2 contains free isocyanate functions in a proportion of 0.544 mol of NCO function per 100 g of Tolonate® HDT LV2 product.

The process is then performed as in the above example, working with 14.8 g of Tolonate HDT LV2.

The same molar ratios are used, i.e. in a ratio of NCO functions/COOH functions of the monoester=1 and a molar ratio of Et$_3$N functions/COOH functions=0.01.

The product obtained is indeed the expected reaction product and has the following major characteristic bands:
absence of an NCO band at 2257 cm$^{-1}$
carbonate C=O band at 1798 cm$^{-1}$
succinate enter C=O band at 1743 cm$^{-1}$
HDT isocyanurate bands at 1687 and 1468 cm$^{-1}$
amide —C=O—NH— band at 1546 cm$^{-1}$ and secondary amide C=O band at 1640 cm$^{-1}$
NH band at 3350-3250 cm$^{-1}$.

Example 9

Synthesis of a Resin Containing Pendent Carbonate Functions and Essentially Isocyanurate Units, Obtained by Reacting the Compound of Example 6 with the Isocyanurate Trimer of Isophorone Diisocyanate (IPDT)

IPDT is a solid product (melting point of 100-115° C.) obtained by cyclopolycondensation of isophorone diisocyanate (IPDI) with itself, containing isocyanurate units and free isocyanate functions. The titer of isocyanate functions is 0.409 mol of NCO functions per 100 g of product.

The process is performed as in the above example, working with 15.1 g of solid IPDT from the company Creanova Huels.

The same molar ratios are used, i.e. in a ratio of NCO functions/COOH functions of the monoester=1 and a molar ratio of the Et$_3$N functions/COOH functions=0.01.

The product obtained is indeed the expected reaction product, but it still contains unreacted isocyanate functions and free acid functions in a proportion of 20 mol % of the initial functions and has the following major characteristic bands:
NCO band at 2257 cm$^{-1}$
carbonate C=O band at 1788 cm$^{-1}$
succinate eater C=O band at 1735 cm$^{-1}$
IPDT isocyanurate bands at 1693 and 1446 cm$^{-1}$
amide —C=O—NH— band at 1546 cm$^{-1}$ and secondary amide C=O band at 1640 cm$^{-1}$
NH band at 3350-3250 cm$^{-1}$
acid OH function at 3200-2500 cm$^{-1}$ Example 10

Synthesis of a Resin Containing Pendent Carbonate Functions, Isocyanate Functions Masked with 1,2,4-triazole and Essentially Isocyanurate Units, Obtained by Reaction of the Compound of Example 6, 1,2,4-triazole and Tolonate® HDT The process is performed as in the above example, using 15 g of Tolonate® HDT (cf. Example 6), 2.797 g of 1,2,4-triazole and 8.77 g of succinic acid glyceryl carbonate monoester. The molar ratio of COOH functions/NCO functions is 0.5, the molar ratio of triazole functions/NCO functions is 0.5 and the molar ratio of Et$_3$N functions/COOH functions is 1%.

The product obtained is indeed the expected reaction product and has the following major characteristic bands:
absence of an NCO band at 2257 cm$^{-1}$
carbonate C=O band at 1788 cm$^{-1}$
succinate ester C=O band plus C=O blocked with triazole at 1739 cm$^{-1}$
HDT isocyanurate bands at 1684 and 1467 cm$^{-1}$
amide —C=O—NH— band observed with difficulty at 1546 cm$^{-1}$ and secondary amide C=O band at 1640 cm$^{-1}$
triazole-blocking bands at 3337, 3126, 1531 and 1506 cm$^{-1}$.

The product obtained thus has 50% of the isocyanate bands in the form temporarily masked with 1,2,4-triazole, which may be regenerated thermally at a temperature of about 130-140° C. The 50 mol % of remaining isocyanate functions were converted into amide bonds by reaction with the acid functions and form the link between the aliphatic chain ((CH$_2$)$_6$) borne by the isocyanurate unit and the succinylcarbonate chain.

This compound is thus characterized by a molar ratio of NCO masked with 1,2,4-triazole/carbonate functions equal to 1.

Example 11

Synthesis of Glutaric Acid Glyceryl Carbonate Monoester

The process is performed as in Example 6, replacing succinic anhydride mole for mole with glutaric anhydride.

Glutaric acid glyceryl carbonate monoester is obtained in the form of a solid compound in a yield of 52%, This product has characteristic infrared bands that are identical to those of the derivative of the compound of Example 6.

The formula of the compound is the following:

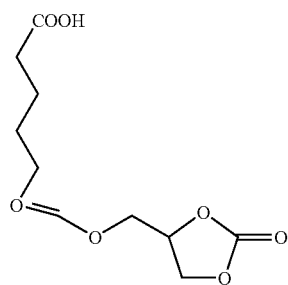

Example 12-15

Synthesis of a Resin Containing Pendent Carbonate Functions and Essentially Isocyanurate Units, Obtained by Reaction of the Compound of Example 11 and Isocyanurate Polyisocyanates The process is performed as for Examples 7 to 10, replacing the compound of Example 6 mole for mole with the compound of Example 11 (glutaric acid glyceryl carbonate monoester).

The products obtained are in accordance with the expected products and are confirmed by infrared analysis.

The major characteristic infrared bands are those indicated for the compounds of Examples 7-10, is respectively.

Example 16

Synthesis of a Resin Containing Pendent Carbonate Functions and Essentially Isocyanurate Units, Obtained by Reaction of Tolonate® HDT, Trimethylol-Propane and Carbonyldiimidazole 1 mol of trimethylolpropane (134 g), 1 mol of carbonyl diimidazole (165 g) and 100 g of Solvesso® 100 are placed in a reactor under an inert atmosphere of nitrogen. The stirred reaction medium is heated at 90° C. for 5 hours.

600 g of Tolonate® HDT are added to the hot reaction mixture and the reaction medium is left stirring at 75° C. overnight. An infrared analysis of the reaction medium indicates that the isocyanate band has virtually disappeared.

The infrared analysis of the product indicates that the expected product is indeed obtained, i.e. a polyisocyanurate resin in which about ⅔ of the isocyanate functions are blocked with imidiazole and about ⅓ of the isocyanate functions are blocked in the form of the carbamate of trimethylolpropane carbonate.

It is thus shown that a thermally crosslinkable resin can be obtained in a single step using a carbonyl compound activated with leaving groups which may be used as temporary protecting groups for isocyanate functions.

Example 17

Synthesis of 9,10-dihydroxystearic acid carbonate 10 g of 9,10-dihydroxystearic acid are introduced into a reactor. A molar amount of normal (1N) sodium hydroxide is added to neutralize all of the carboxylic functions in the form of the sodium salt. 100 ml of N,N-dimethylformamide are added and the mixture is stirred at 80° C. for one hour. 90% of the solvent is then evaporated off under vacuum to remove all of the water.

100 ml of dry N,N-dimethylformamide and 5.22 g of carbonyldiimidazole are then added and the mixture in stirred at 80° C. overnight under a stream of nitrogen.

The product is then concentrated to dryness on a rotary evaporator under vacuum to remove 95% of the N,N-dimethylformamide.

An acidic aqueous solution is added to the product to convert the sodium salt into the corresponding acid, such that the value measured with pH paper is 2. The acid carbonate is then extracted three times with 180 ml of toluene.

The organic toluene phases are combined and the solvent is evaporated off under vacuum to give 12.3 g of a pasty product.

The structure of the product is confirmed by $^1$H NMR analysis (DMSO).

The presence of the carbonate function and of the carboxylic acid function are indeed confirmed.

The formula of the compound is the following:

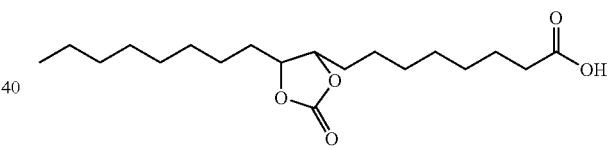

Example 18

Synthesis of a Resin Containing Pendent Carbonate Functions and Isocyanurate Units Tolonate® HDT (0.518 mol of NCO function per 100 g of product) and 12 g of 9,10-dihydroxystearic acid carbonate, ouch that the molar ratio of NCO functions/COOH functions is equal to 1, are placed in a reactor. 1 mol % of triethylamine relative to the carboxylic acid COOH functions is added. The mixture is left stirring at 95° C. for 8 hours under a stream of nitrogen.

The product obtained is in accordance with the expected product. It has the following characteristic bands:

no NCO band at 2257 cm$^{-1}$ carbonate C=O band at 1788 cm$^{-1}$ succinate ester C=O band at 1739 cm$^{-1}$ HDT isocyanurate bands at 1685 and 1466 cm$^{-1}$ amide —C=O—NH— band at 1546 cm$^{-1}$ and secondary amide C=O band at 1640 cm$^{-1}$ NH band at 3350-3250 cm$^{-1}$

Example 19

Synthesis of 1,9,10-trihydroxyoctadecane

The procedure disclosed in U.S. Pat. No. 2,443,280 of Jun. 15 1948 is used, using 100 g of oleyl alcohol as starting material.

The product is recovered in a yield of 25%.

Example 20

Synthesis of a Thermally Crosslinkable Urethan Resin Containing Masked Isocyanate Functions and Pendent Carbonate Functions 0.1 mol of the compound 1,9,10-trihydroxy-octadecane of Example 19 and 100 ml of 2-(1-methoxy propyl)acetate are placed in a reactor equipped with a stirrer and under an atmosphere of nitrogen. 0.1 mol of Tolonate HDT, whose NCO titer is 0.518 mol per 100 g, is then added to the reaction medium. The temperature of the reaction medium is brought to a temperature of between 45 and 50° C. After reaction for one hour with stirring, 0.12 mol of carbonyldiimidazole is added. The reaction medium is stirred at 50° C. for 4 hours and is then brought to a temperature of about 85° C. and left stirring overnight.

The reaction medium is then left to cool so as to give a viscous composition of a urethane resin which is characterized by the absence of free isocyanate functions and by the presence of isocyanate functions masked with imidazole, carbamate functions and predominantly cyclic carbonate functions.

The infrared analysis indicates the presence of the following characteristic bands:
- absence of an NCO band at 2257 $cm^{-1}$
- carbonate C=O band at 1785 $cm^{-1}$
- carbamate band (1720 $cm^{-1}$) and imidazole-blocking band at about 1735 $cm^{-1}$
- HDT isocyanurate bands at 1691 and 1467 $cm^{-1}$.

Example 21

Preparation of a Prepolymer Containing Free Isocyanate End Functions

The following are successively introduced into a three-necked reactor:
- 100 g of K-Flex 188 aliphatic polyol (polyester from King Industries) (6.97% OH/100 g, i.e. 0.41 mol OH/100 g);
- 1680 g of HDI (5 mol).

The reaction medium is heated at 80° C. It is stirred under $N_2$ at 80° C. for five hours and the excess HDI is then removed by distillation under high vacuum.

The product obtained is a urethane prepolymer containing isocyanate end functions which has an NCO titer of 0.22 mol NCO per 100 g, i.e. 9.24% NCO per 100 g of product.

Example 22

Synthesis of a Prepolymer Containing Amino End Functions 150 g of prepolymer containing NCO end functions of Example 21 are introduced into a reactor with stirring and placed under an inert atmosphere of nitrogen.

0.33 mol of 5-amino-1-pentanol hydrochloride and 600 g of toluene are added.

The reaction medium is heated at 60° C., in the presence of 0.1% dibutyltin dilaurate, until the NCO titer is less than 1% (method of assaying the NCO functions by reaction with dibutylamine and assay of the residual amine with HCl).

A viscous toluene solution of prepolymer containing amine hydrochloride functions, whose $NH_2$ titer is about 0.04 mol $NH_2$/100 g, is obtained.

Example 23

Formation of a Coating 100 g of the polymer solution of Example 22 (0.04 mol of amine functions in hydrochloride form) are introduced into a reactor equipped with a stirrer. 20 g of the product of Example 3 are then added, such that the molar ratio of amine functions/O—C(=O)—O— functions is equal to 1. 0.04 mol of triethylamine and 200 g of toluene are added.

The mixture is stirred for 30 minutes at room temperature.

The mixture obtained is placed on a glass plate so as to form a film 50 µm thick, and is then placed in an oven at 50° C. for 30 minutes, then at 100° C. for 20 minutes and at 140° C. for 30 minutes.

After firing, a transparent crosslinked coating which has good mechanical properties is obtained.

This example shows that the products of the invention allow coatings to be obtained.

However, an optimization of the formulation conditions (choice of solvent, mixture with other polyols or other amines, optimization of the ratios (NCO/OH), (amines/O—C(=O)—O— functions), nature of the acrylic polyol or polyester, nature of the isocyanates used) makes it possible to adapt the properties of the coatings to the desired needs.

Example 24

Synthesis of HDT Protected with Imidazole and Trimethylolpropane Carbonate

The following are added to a reactor:
- 134 g of trimethylolpropane (1 mol)
- 1 mol of carbonyldiimidazole (165 g) and the reaction mixture is then heated at 80° C. for five hours.
- 600 g of HDT are added to the hot reaction mixture, which is then stirred at 80° C. for five hours until the NCO band disappears.

900 g of a Tolonate HDT derivative, ⅔ of the NCO functions of which are protected with imidazole and ⅓ of which are protected with glyceryl carbonate, are thus obtained directly in a single operation.

It is thus shown that this derivative can be obtained in a single operation using a carbonyl derivative activated with leaving groups (imidazole, triazole, phenyl) which may subsequently serve as agents for masking the NCO function.

The invention claimed is:

1. Modified stable polyisocyanates of formula (I) below having a crosslinking functional group:

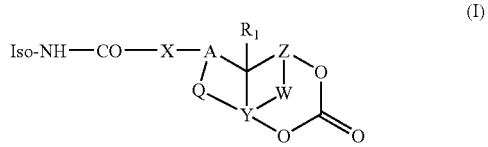

in which:
iso is a polyisocyanate residue containing at least two isocyanate functions after conversion of at least one isocyanate function, and further comprising at least one other isocyanate function masked with a masking agent or a mixture of thermolabile masking agents: and iso optionally comprising at least one additional unmodified isocyanate function;
X represents an atom or a group of atoms resulting from the reaction of a compound bearing a —XH group, optionally after decarboxylation, with an isocyanate function;
A represents a bond or a linear, branched or cyclic hydrocarbon-based chain containing from 1 to 30 carbon atoms;
$R_1$ represents H or a $C_1$-$C_6$ alkyl group;
Q is absent or represents an oxygen or sulfur atom or a hydrocarbon-based chain as defined for A;
Z represents a bond or a hydrocarbon-based chain as defined for A;
Y represents a bond or a hydrocarbon-based chain as defined for A;
W is absent or represents a bond, an oxygen or sulfur atom or a hydrocarbon-based chain as defined for A; and
Q being absent when Y or A represents a bond and W or A being absent when Y or Z represents a bond;
with the proviso that Z and Y do not simultaneously represent a bond.

2. Modified stable polyisocyanates according to claim 1, in which X is selected from the group consisting of:
—O
—S
=M
=NR, in which R represents a hydrogen atom or an optionally substituted hydrocarbon-based group containing from 1 to 12 carbon atoms, optionally interrupted with at least one hetero atom or hetero group,

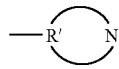

in which R' represents a 4- to 10-membered optionally substituted hydrocarbon chain optionally interrupted with at least one hetero atom or hetero group, the chain R' forming with NH a nitrogen ring,

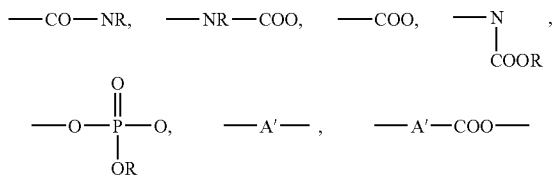

wherein A' is an optionally substituted hydrocarbon-based chain comprising from 1 to 12 carbon atoms, optionally interrupted with at least one hetero atom or hetero group,
—NH—CO—NH, and
—NH—CO—NR, wherein R is as defined above.

3. Modified stable polyisocyanates according to claim 1, wherein X represents an oxygen atom.

4. Modified stable polyisocyanates according to claim 1, wherein A represents a —$CH_2$— group.

5. Modified stable polyisocyanates according to claim 1, wherein Y represents a —$CH_2$— group.

6. Modified stable polyisocyanates according to claim 1, wherein Z represents a bond or —$CH_2$—.

7. Modified stable polyisocyanates according to claim 1, wherein W and Q represent a bond.

8. Modified stable polyisocyanates according to claim 1, wherein said crosslinking functional group comprises a cyclic carbonate formed by reaction of a vicinal hydroxy compound, with an activated carbonylating agent.

9. Modified stable polyisocyanates according to claim 8, wherein the vicinal hydroxy compound is chosen from glycerol, 9,10-dihydroxystearic acid, 1,9,10-trihydroxy-octadecane or trimethylolpropane.

10. Modified stable polyisocyanates according to claim 8, wherein the activated carbonylating agent is chosen from carbonyldiimidazole, carbonylbis(1,2,4-triazole), carbonylbis(methyl ethyl ketoxime) or N,N'-disuccinimidyl carbonate.

11. Modified stable polyisocyanates according to claim 1, wherein said crosslinking functional group is derived from glyceryl carbonate, succinic acid glyceryl carbonate monoester, glutaric acid glyceryl carbonate monoester, trimethylol propane carbonate, 9,10-dihydroxystearic acid carbonate or 1,9,10-trihydroxy-octadecane carbonate.

12. Modified stable polyisocyanates according to claim 1, wherein the crosslinking functional group is obtained by reacting an isocyanate function with glyceryl carbonate or a fatty acid carbonate or ester thereof.

13. Modified stable polyisocyanates according to claim 1, of the formula:

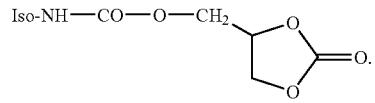

14. Modified stable polyisocyanates according to claim 1, wherein the masking agent is selected from lactams or oximes or optionally substituted imidazoles, pyrazoles, 1,2,3-triazole, 1,2,4-triazole or phenols.

15. Modified stable polyisocyanates according to claim 1, wherein the unmodified isocyanate function(s) are masked by at least two different masking agents.

16. Modified stable polyisocyanates according to claim 1, wherein at least two different masking agents are selected such that, in the octanol test at 110° C., the ratio $$D = \frac{\text{percentage of masking agent unblocking first at } 110° \text{ C.}}{\text{percentage of masking agent unblocking last at } 110° \text{ C.}}$$

is greater than 4/3.

17. Modified stable polyisocyanates according to claim 16, wherein the masking agents are an oxime and a triazole.

18. Modified stable polyisocyanates according to claim 1, derived from polyisocyanates selected from the group consisting of:
compounds having at least one isocyanurate group,
compounds having at least one uretidinedione group,
compounds having at least one carbamate group,
compounds having at least one allophanate group,
compounds having at least one ester group,
compounds having at least one urea function,
compounds having at least one iminocyclooxadiazinedione function, compounds having at least one cyclooxadiazinetrione function, compounds having at least one masked isocyanate group, and compounds comprising a combination of at least one of the aforementioned groups.

19. Modified stable polyisocyanates according to claim 1, wherein at least one compound containing at least three isocyanate functions is reacted with a compound of formula II:

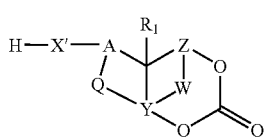

(II)

in which X' represents X or X—COO, X being as specified above, and wherein at least 1% up to 99% by weight, of said isocyanate functions are masked with at least one masking group and from 0 to 99% by weight, are free isocyanate functions.

20. Modified polyisocyanates according to claim 19, further including diisocyanate derivatives wherein at least some of the isocyanate functions are modified with a compound of formula II, and at least 1% by weight, of isocyanate functions are modified with at least one masking group.

21. Modified polyisocyanates according to claim 1, comprising mixtures of polyfunctional isocyanate tricondensates derived from the (cyclo)trimerization of three isocyanate monomer molecules and optionally other monomers and comprising an isocyanurate and/or biuret ring and/or allophanates, and/or dimers wherein at least some of the isocyanate functions are modified with said crosslinking functional group.

22. Modified polyisocyanates according to claim 1, comprising physical mixtures of polyfunctional isocyanate tricondensates, with allophanates, uretidinediones or dimers, wherein said modified polyisocyanates comprise from 100% to 1% by weight of isocyanate functions masked with a masking group.

23. Modified stable polyisocyanates according to claim 19, comprising isocyanates modified with a compound of formula II having free isocyanate groups and masked isocyanate groups and allophanate and/or uretidinedione groups.

24. Process for preparing a modified polyisocyanate according to claim 1, having masked isocyanate functions, the process comprising:

a₁) reaction of a polyisocyanate having at least three isocyanate functions and optionally having a group selected from carbamate, urea, biuret, uretidinedione, isocyanate, urethane or allophanate, with a compound of general formula II:

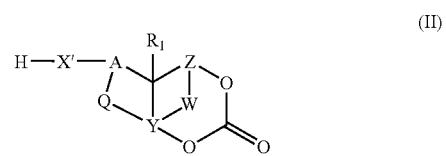

(II)

in which $R_1$, A, Q, Y, Z and W have the same meanings as above, and X' represents X or X—COO, X being as specified above; and b) successively reacting with at least one masking compound;

or a₂) simultaneous reaction of said polyisocyanate with a compound of formula II and at least one masking compound; and c) isolation of the product obtained.

25. Polyisocyanate compositions consisting essentially of a mixture comprising at least 1% and not more than 99% of a modified stable polyisocyanate according to claim 1, bearing said crosslinking functional group and at least 1% and not more than 99% of another polyisocyanate modified stable polyisocyanate according to claim 1, bearing said crosslinking functional group and/or another molecule derived from a diisocyanate bearing free and/or masked isocyanate functions and containing no crosslinking functional groups.

26. A method for the preparation of nonexpanded coatings, comprising using as a reactant an effective amount of the compound according to claim 1.

27. A method for the preparation of nonexpanded coatings, comprising using as a reactant an effective amount of the compound according to claim 1 to form crosslinkable prepolymers, after opening the crosslinking functional group with a reagent.

28. A method for the preparation of nonexpanded coatings according to claim 27, wherein the reagent is chosen from compounds with alcohol functions, primary or secondary amine functions, heterocyclic nitrogen compounds containing a reactive hydrogen atom, oximes or phenols.

29. A method for the preparation of nonexpanded coatings according to claim 27, wherein the reagent is chosen from aqueous ammonia, primary or secondary amines, nitrogen heterocycles or salts thereof.

30. Polymers and/or reticulates obtained by reaction of the modified stable polyisocyanates as claimed in claim 1.

31. A method for the preparation of polycondensates and reticulates useful as coatings, comprising reacting an effective amount of a modified stable polyisocyanate as claimed in claim 1 with at least one nucleophilic co-reagent.

32. A method according to claim 31, wherein the nucleophilic co-reagent comprises at least one amine.

33. A method according to claim 32, wherein the amine comprises a di- or poly-amine.

34. Composition comprising modified stable polyisocyanates as claimed in claim 1, together with at least one compound containing labile hydrogen.

* * * * *